(12) United States Patent
Gupta et al.

(10) Patent No.: US 7,888,099 B2
(45) Date of Patent: Feb. 15, 2011

(54) METHODS FOR PRODUCING A SYNCHRONIZED POPULATION OF CONIFER SOMATIC EMBRYOS

(75) Inventors: Pramod K. Gupta, Federal Way, WA (US); Diane Holmstrom, Sumner, WA (US); Bonnie Larson, Granite Falls, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 65 days.

(21) Appl. No.: 10/636,081

(22) Filed: Aug. 6, 2003

(65) Prior Publication Data

US 2004/0096970 A1    May 20, 2004

Related U.S. Application Data

(60) Provisional application No. 60/426,767, filed on Nov. 14, 2002.

(51) Int. Cl.
*A01H 4/00* (2006.01)
*A01H 1/00* (2006.01)

(52) U.S. Cl. .............. 435/240.45; 435/240.48; 435/240.49; 435/240.46; 435/240.54; 47/58; 800/200

(58) Field of Classification Search .............. 435/422, 435/240.45, 240.48, 240.46; 47/58; 800/200
See application file for complete search history.

(56) References Cited

U.S. PATENT DOCUMENTS

| | | | |
|---|---|---|---|
| 4,217,730 A | 8/1980 | Abo El-Nil | |
| 4,801,545 A | 1/1989 | Stuart et al. | |
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,183,757 A | 2/1993 | Roberts | |
| 5,187,092 A | 2/1993 | Uddin | |
| 5,236,841 A | 8/1993 | Gupta | |
| 5,238,835 A | 8/1993 | McKersie et al. | |
| 5,294,549 A * | 3/1994 | Pullman et al. ............. | 435/422 |
| 5,413,930 A | 5/1995 | Becwar et al. | |
| 5,464,769 A | 11/1995 | Attree et al. | |
| 5,482,857 A | 1/1996 | Gupta et al. | |
| 5,491,090 A | 2/1996 | Handley, III et al. | |
| 5,501,972 A | 3/1996 | Westcott | |
| 5,506,136 A | 4/1996 | Becwar et al. | |
| 5,523,230 A | 6/1996 | Smith | |
| 5,534,433 A | 7/1996 | Coke | |
| 5,534,434 A | 7/1996 | Coke | |
| 5,563,061 A * | 10/1996 | Gupta ......................... | 435/422 |
| 5,564,224 A | 10/1996 | Carlson et al. | |
| 5,565,355 A | 10/1996 | Smith | |
| 5,587,312 A | 12/1996 | van Holst et al. | |
| 5,610,051 A | 3/1997 | Becwar et al. | |
| 5,677,185 A | 10/1997 | Handley, III | |
| 5,731,191 A | 3/1998 | Rutter et al. | |
| 5,731,203 A | 3/1998 | Handley, III | |
| 5,731,204 A | 3/1998 | Rutter et al. | |
| 5,821,126 A | 10/1998 | Durzan et al. | |
| 5,840,581 A | 11/1998 | Carraway et al. | |
| 5,850,032 A | 12/1998 | Wann | |
| 5,856,191 A | 1/1999 | Handley, III | |
| 5,985,667 A | 11/1999 | Attree et al. | |
| 6,022,744 A | 2/2000 | Tetteroo et al. | |
| 6,117,678 A | 9/2000 | Carpenter et al. | |
| 6,134,830 A | 10/2000 | Welty | |
| 6,150,167 A | 11/2000 | Carpenter et al. | |
| 6,180,405 B1 | 1/2001 | Aitken-Christie et al. | |
| 6,200,809 B1 | 3/2001 | Klimaszewska et al. | |
| 6,340,594 B1 | 1/2002 | Attree et al. | |
| 6,372,496 B1 | 4/2002 | Attree et al. | |
| 6,417,001 B2 | 7/2002 | Aitken-Christie et al. | |
| 6,444,467 B1 | 9/2002 | Fan et al. | |
| 6,492,174 B1 | 12/2002 | Pullman et al. | |
| 2002/0012994 A1 | 1/2002 | Aitken-Christie et al. | |
| 2002/0092037 A1 | 7/2002 | Connett-Porceddu et al. | |
| 2002/0100083 A1 | 7/2002 | Connett-Porceddu et al. | |

FOREIGN PATENT DOCUMENTS

| | | |
|---|---|---|
| EP | 0 300 730 B1 | 1/1989 |
| EP | 0 618 766 B1 | 10/1994 |
| EP | 0 934 691 A2 | 8/1999 |
| FI | 20030819 | 5/2002 |
| WO | 95/05070 A1 | 2/1995 |

(Continued)

OTHER PUBLICATIONS

Hansen et al. "Recent advances in the transformation of plants," Trends in Plant Science Reviews, Jun. 1999, vol. 4, No. 6, pp. 226-231.*

(Continued)

*Primary Examiner*—Annette H Para
(74) *Attorney, Agent, or Firm*—Christensen O'Connor Johnson Kindness PLLC

(57) ABSTRACT

In one aspect, the present invention provides methods for producing conifer somatic embryos. The methods of this aspect of the invention each include the steps of cultivating conifer embryogenic cells in, or on, a synchronization medium that comprises an absorbent composition and at least one synchronization agent selected from the group consisting of abscisic acid and a gibberellin. Some embodiments of the methods provide a synchronized population of conifer somatic embryos wherein at least about 50% of the embryos are at about the same developmental stage. Some embodiments of the methods of the invention yield at least 100% more cotyledonary somatic embryos than an identical method for producing conifer somatic embryos that does not utilize a synchronization medium comprising an absorbent composition and at least one synchronization agent selected from the group consisting of abscisic acid and a gibberellin.

21 Claims, No Drawings

FOREIGN PATENT DOCUMENTS

| WO | 9505070 | 2/1995 |
| --- | --- | --- |
| WO | WO 95/33822 A1 | 12/1995 |
| WO | WO 98/48279 A1 | 10/1998 |
| WO | WO 99/46977 | 9/1999 |
| WO | WO 01/20972 A1 | 9/2000 |

OTHER PUBLICATIONS

Nagmani, R., et al., "Anatomical Comparison of Somatic and Zygotic Embryogeny in Conifers," in S.M. Jain et al. (eds.), vol. 1, Somatic Embryogenesis in Woody Plants, Series: Forestry Sciences, vol. 44, 1995, pp. 23-48.

Mathur, G. et al., "Studies on Somatic Embryogenesis From Immature Zygotic Embryos of CHIR Pine (*Pinus roxburghii* Sarg.)," *Current Science* 79(7):999-1004, 2000.

von Aderkas, P., et al., "Charcoal Affects Early Development and Hormonal Concentrations of Somatic Embryos of Hybrid Larch," *Tree Physiology* 22:431-434, 2002.

Keinonen-Mettälä, K., et al., "Somatic Embryogenesis of *Pinus sylvestris*," *Scand. J. For. Res. 11*:242-250, 1996.

Attree, S.M. et al., "Somatic Embryo Maturation, Germination, and Soil Establishment of Plants of Black and White Spruce (*Picea mariana* and *Picea glauca*)," *Can. J. Bot. 68*:2583-2589, 1990.

Attree, S.M., et al., "Initiation of Embryogenic Callus and Suspension Cultures, and Improved Embryo Regeneration of Protoplasts, of White Spruce (*Picea glauca*)," *Can. J. Bot. 67*:1790-1795, 1989.

Attree, S.M., et al., "Plantlet Regeneration From Embryogenic Protoplasts of White Spruce (*Picea glauca*)," *Bio/Technology 7*:1060-1062, 1989.

Boulay, M.P., et al., "Development of Somatic Embryos From Cell Suspension Cultures of Norway Spruce (*Picea abies* Karst.)," *Plant Cell Reports 7*:134-137, 1988.

Cornu, D. and C. Geoffrion, "Aspects of Somatic Embryogenesis in Larch Trees," *Bull. Soc. Bot. Fr.*, 137 Actual. Bot. (¾):25-34, 1990 [translation].

Gupta, P.K., et al., "Scale-Up Somatic Embryogenesis of Conifers for Reforestation," *Proceedings of the 3rd Canadian Workshop on Plant Tissue Culture and Genetic Engineering, University of Guelph, Symposium 1: Somatic Embryogenesis and Synthetic Seeds*, Abstract, Jun. 1992.

Hakman, I. and L.C. Fowke, "An Embryogenic Cell Suspension Culture of *Picea glauca* (White Spruce)," *Plant Cell Reports 6*:20-22, 1987.

Krogstrup, P. "Somatic Embryogenesis in Sitka Spruce (*Picea sitchensis* (Bong.) Carr.)," *Plant Cell Reports 7*:594-597, 1988.

Lelu, M.A. et al., "Effect of Maturation Duration on Desiccation Tolerance in Hybrid Larch (*Larix X leptoeuropaea dengler*) Somatic Embryos," *In Vitro Cell. Dev. Biol. 31*15-20, 1995.

Lu, C.-Y. and T.A. Thorpe, "Somatic Embryogenesis and Plantlet Regeneration in Cultured Immature Embryos of *Picea glauca*," *J. Plant Physiol. 128*:297-302, 1987.

Norgaard, J.V., and P. Krogstrup, "Cytokinin Induced Somatic Embryogenesis From Immature Embryos of *Abies nordmanniana* Lk.," *Plant Cell Reports 9*:509-513, 1991.

Roberts, D.R., "Abscisic Acid and Mannitol Promote Early Development, Maturation and Storage Protein Accumulation in Somatic Embryos of Interior Spruce," *Physiologia Plantarum 83*:247-254, 1991.

Roberts, D.R., et al., "Interaction Between Maturation and High Relative Humidity Treatments and Their Effects on Germination of Sitka Spruce Somatic Embryos," *J. Plant Physiol. 138*:1-6, 1991.

Roberts, D.R., et al., "Synchronous and High Frequency Germination of Interior Spruce Somatic Embryos Following Partial Drying at High Relative Humidity," *Can. J. Bot. 68*:1086-1090, 1989.

Thompson, R.G. and P. von Aderkas, "Somatic Embryogenesis and Plant Regeneration From Mature Embryos of Western Larch," *Plant Cell Reports 11*:379-386, 1992.

Timmis, R., "Bioprocessing for Tree Production in the Forest Industry: Conifer Somatic Embryogenesis," *Biotechnol. Prog. 14*(1):156-166, 1998.

von Arnold, S. and I. Hakman, "Regulation of Somatic Embryo Development in *Picea abies* by Abscisic Acid (ABA)," *J. Plant Physiol. 132*:164-169, 1988.

von Arnold, S. and T. Eriksson, "A Revised Medium for Growth of Pea Mesophyll Protoplasts," *Physiol. Plant 39*:257-260, 1977.

Webb, D.T., et al., "Factors Influencing the Induction of Embryogenic and Caulogenic Callus From Embros of *Picea glauca* and *P. engelmanii*," *Can. J. For. Res. 19*:1303-1308, 1989.

Taber RP et al., "Kinetics of Douglas-fir (*Pseudotsunga menziesii*) somatic embryo development," *Can J Bot* (76): 838-871, 1998.

* cited by examiner

METHODS FOR PRODUCING A SYNCHRONIZED POPULATION OF CONIFER SOMATIC EMBRYOS

CROSS REFERENCE TO RELATED APPLICATION

The present application claims the benefit of U.S. Provisional Application No. 60/426,767, filed Nov. 14, 2002.

FIELD OF THE INVENTION

The present invention relates to methods for producing plant embryos in vitro, and optionally producing plants from the plant embryos.

BACKGROUND OF THE INVENTION

The demand for coniferous trees, such as pines and firs, to make wood products continues to increase. One proposed solution to this problem is to identify individual trees that possess desirable characteristics, such as a rapid rate of growth, and produce numerous, genetically identical, clones of the superior trees by somatic cloning.

Somatic cloning is the process of creating genetically identical trees from tree tissue other than the male and female gametes. In one approach to somatic cloning, plant tissue is cultured in an initiation medium which includes hormones, such as auxins and/or cytokinins, that initiate formation of embryogenic cells that are capable of developing into somatic embryos. The embryogenic cells are then further cultured in a maintenance medium that promotes multiplication of the embryogenic cells. The multiplied embryogenic cells are then cultured in a development medium that promotes development of conifer somatic embryos which can, for example, be placed within artificial seeds and sown in the soil where they germinate to yield conifer seedlings. The seedlings can be transplanted to a growth site for subsequent growth and eventual harvesting to yield lumber, or wood-derived products.

A continuing problem with somatic cloning of conifer embryos is stimulating efficient formation of conifer somatic embryos that are capable of germinating to yield conifer plants. Preferably conifer somatic embryos, formed in vitro, are physically and physiologically similar, or identical, to conifer zygotic embryos formed in vivo in conifer, seeds. A particular problem affecting conifer somatic embryogenesis is the asynchronous development of somatic embryos from cultures of embryogenic cells. This asynchrony in development results in cultures in which embryos are at disparate stages of development, greatly reducing the overall efficiency of the process. There is therefore a continuing need for methods for producing conifer somatic embryos from conifer embryogenic cells. The present invention provides methods that satisfy this need.

SUMMARY OF THE INVENTION

In one aspect, the present invention provides methods for producing a synchronized population of conifer somatic embryos. The methods of the invention each include the step of cultivating conifer embryogenic cells in, or on, a synchronization medium that comprises an absorbent composition and at least one synchronization agent selected from the group consisting of abscisic acid and a gibberellin, wherein the absorbent composition and the at least one synchronization agent are present at a concentration effective to produce a synchronized population of conifer somatic embryos.

In some embodiments, the absorbent composition in the synchronization medium is activated charcoal. The concentration of the absorbent composition may be from about 0.5 g/L to about 50 g/L, such as from about 0.5 g/L to about 25 g/L or from about 0.5 g/L to about 5.0 g/L. The concentration of the abscisic acid in the synchronization medium may be from about 1.0 mg/L to about 500 mg/L, such as from about 1.0 g/L to about 50 g/L or from about 0.5 g/L to about 10 g/L. The concentration of the one or more gibberellin(s) in the synchronization medium may be from about 0.5 mg/L to about 500 mg/L. In some embodiments, the conifer embryogenic tissue is cultured in, or on, the synchronization medium for a period of from about 0.5 weeks to about 5 weeks.

The methods of the invention provide a synchronized population of conifer somatic embryos. In some embodiments, the methods of the invention provide a synchronized population of conifer somatic embryos in which at least 50% of the embryos are at the same developmental stage.

The methods of the invention produce a higher yield of conifer somatic embryos than an equivalent method in which the embryogenic cells are not cultivated in a synchronization medium. Thus, some embodiments of the methods of the invention yield at least 100% more conifer somatic embryos (such as at least 150% more conifer somatic embryos, or such as at least 200% more conifer somatic embryos) than an identical method for producing conifer somatic embryos that does not include the step of cultivating conifer embryogenic cells in, or on, a synchronization medium that comprises an absorbent composition and at least one synchronization agent selected from the group consisting of abscisic acid and gibberellins.

The methods of the present invention are useful, for example, for preparing conifer somatic embryos that can be further characterized, such as by genetic or biochemical means, and/or can be germinated to yield conifer plants that can be grown into mature conifer trees, if so desired. Thus, for example, the methods of the invention can be used to produce clones of individual conifer trees that possess one or more desirable characteristics, such as a rapid growth rate or improved wood quality. For example, a population of conifer somatic embryos of the invention can be used to produce a stand, or forest, of conifer trees possessing one or more desirable characteristics, such as a rapid growth rate or improved wood quality. The trees can be utilized to produce wood products.

DETAILED DESCRIPTION OF THE PREFERRED EMBODIMENT

Unless specifically defined herein, all terms used herein have the same meaning as they would to one skilled in the art of the present invention.

As used herein, the terms "embryogenic cells" refers to any cells, including cells that are organized to form a tissue or an organ, derived from a plant of the order Coniferales, that are capable of producing one or more conifer somatic embryos when treated in accordance with the methods of the invention. Thus, the term. "embryogenic cells" includes, for example, conifer embryonal suspensor masses.

As used herein, the term "cotyledonary embryo" refers to an embryo that possesses at least one cotyledon. The term "pre-cotyledonary embryo" refers to an embryo that does not possess any cotyledons.

Unless stated otherwise, all concentration values that are expressed as percentages are weight per volume percentages.

In one aspect, the present invention provides methods for producing synchronized populations of conifer somatic embryos. The methods comprise the step of culturing conifer embryogenic cells in, or on, a synchronization medium containing an absorbent composition and at least one synchronization agent selected from the group consisting of abscisic acid and a gibberellin, wherein the absorbent composition and the at least one synchronization agent are present at a concentration effective to produce a synchronized population of conifer somatic embryos. The methods of the invention can be used to produce synchronized somatic embryos from any member of the order Coniferales, such as Douglas fir, Norway spruce, species of the genus *Abies* (e.g., Noble fir), and members of the genus *Pinus*, such as Loblolly pine (*Pinus taeda*).

An example of embryogenic cells useful in the practice of the present invention are embryonal suspensor masses (ESMs). ESMs can be prepared, for example, from pre-cotyledonary embryos removed from seed. For example, the seed are surface sterilized before removing the pre-cotyledonary embryos which are then cultured on, or in, an induction medium that promotes formation of ESMs, which include early stage embryos in the process of multiplication by budding and cleavage. A representative example of an induction medium is medium $BM_1$ described in EXAMPLE 1 of the present application.

Cleavage polyembryony (embryonal suspensor mass proliferation) continues in cultures after plating onto development medium, and new embryos are beginning to develop even after eight to ten weeks of culture on development medium. Due to this continuing cleavage, embryos are not uniform in stage, shape, size, or quality within a single plate. This lack of uniformity detrimentally affects the efficiency of somatic cloning of conifers. The present invention addresses the problem of unsynchronized development of conifer embryogenic cells, including ESMs, by culturing the embryonic cells in, or on, a synchronization medium that causes the majority of embryos in a population of conifer somatic embryos to progress through successive developmental stages together to yield a synchronized population of mature conifer somatic embryos/that can be germinated to form conifer plants.

The synchronization medium contains an absorbent composition and at least one synchronization agent selected from the group consisting of abscisic acid and a gibberellin, wherein the absorbent composition and the at least one synchronization agent are present at a concentration effective to produce a synchronized population of conifer somatic embryos.

The synchronization medium may be a solid medium, or a liquid medium. The osmolality of the synchronization medium is typically in the range of 180-400 mM/kg. The synchronization medium typically also contains nutrients that sustain the embryogenic cells. It is generally desirable, though not essential, to include maltose as the sole, or principal, metabolizable sugar source in the synchronization medium. Useful maltose concentrations are within the range of from about 1% to about 2.5%.

The synchronization medium contains an absorbent composition. The absorbent composition can be any composition that is not toxic to the embryogenic cells at the concentrations utilized in the practice of the present methods, and that is capable of absorbing growth-promoting hormones, and toxic compounds produced by the plant cells that are present in the medium. Thus, the absorbed hormone(s) is/are no longer available to promote the growth of the embryogenic cells in, or on, the medium; and the absorbed toxins cannot adversely affect the plant cells. In this context, the term "absorbing" encompasses any chemical or physical interaction between the absorbent composition and one or more growth-promoting hormones, and/or toxins, in the medium, so that the growth-promoting hormone(s), and/or toxins, are bound to the absorbent composition.

Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from 0.1 g/L to 50 g/L. In some embodiments, the absorbent composition is present in an amount of from 0.5 g/L to 5 g/L, or from about 0.5 g/L to about 1.0 g/L. In those embodiments of the methods of the invention in which more than one absorbent composition is present in the synchronization medium, the foregoing concentration ranges refer to the total absorbent composition concentration in the medium.

The synchronization medium also includes abscisic acid and/or at least one gibberellin (i.e., either or both of the foregoing agents)

Abscisic acid is a sesquiterpenoid plant hormone that is implicated in a variety of plant physiological processes (see, e.g., Milborrow (2001) *J. Exp. Botany* 52: 1145-1164; Leung & Giraudat (1998) *Ann. Rev. Plant Physiol. Plant Mol. Biol.* 49: 199-123). In some embodiments of the methods of the invention, the concentration of abscisic acid in the synchronization medium is between 0.5 mg/L and 500 mg/L. In some embodiments of the methods of the invention, the concentration of abscisic acid in the synchronization medium is between 1 mg/L and 100 mg/L. In some embodiments of the methods of the invention, the concentration of abscisic acid in the synchronization medium is between mg/L and 50 mg/L.

Gibberellins are a class of art-recognized, diterpenoid plant hormones (see, e.g., Krishnamoorthy (1975) Gibberellins and Plant Growth, John Wiley & Sons). Representative examples of gibberellins useful in the practice of the present invention include gibberellic acid, gibberellin 4 and gibberellin 7 which are each disclosed, for example, in the aforementioned Krishnamoorthy text book. An example of a useful mixture of gibberellins is a mixture of gibberellin 4 and gibberellin 7 (referred to as gibberellin 4/7), such as the gibberellin 4/7 sold by Abbott Laboratories, Chicago, Ill.

In some embodiments of the methods of the invention, the concentration of gibberellin(s) in the synchronization medium is between 0.5 mg/L and 500 mg/L. In some embodiments of the methods of the invention, the concentration of gibberellin(s) in the synchronization medium is between 1 mg/L and 100 mg/L. In some embodiments of the methods of the invention, the concentration of gibberellin(s) in the synchronization medium is between 5 mg/L and 50 mg/L. In those embodiments of the methods of the invention in which more than one gibberellin is present in the synchronization medium, the foregoing concentration ranges refer to the total gibberellin concentration in the synchronization medium.

An example of a suitable synchronization medium is medium $BM_3$ set forth in EXAMPLE 1 herein In some embodiments of the methods of the invention, conifer embryogenic cells are cultured in, or on, a synchronization medium that includes an absorbent composition and at least one synchronization agent for a period of from 0.5 weeks to 5 weeks, such as from one week to three weeks, or such as from one week to two weeks. In some embodiments of the methods of the invention, conifer embryogenic cells are cultured in, or on, a synchronization medium that includes an absorbent composition and at least one synchronization agent at a temperature of from 10° C. to 30° C., such as from 15° C. to 25° C., or such as from 20° C. to 23° C.

In some embodiments, the present invention provides methods for producing a synchronized population of conifer somatic embryos, the methods each including the steps of: (a) culturing embryogenic cells in, or on, a synchronization medium that comprises an absorbent composition and at least one synchronization agent selected from the group consisting of abscisic acid and a gibberellin, wherein the absorbent composition and the synchronization agent(s) is/are present at a concentration effective to produce a synchronized culture of pre-cotyledonary conifer somatic embryos; and (b) culturing the synchronized pre-cotyledonary embryos produced in step (a) in, or on, a development medium to yield conifer cotyledonary somatic embryos.

The embryogenic cells are cultured in, or on, a synchronization medium as described above, to yield a synchronized population of pre-cotyledonary embryos. The synchronized pre-cotyledonary embryos are transferred to a development medium for synchronized cotyledonary embryo development. The development medium is typically a solid medium, although the development medium can be a liquid medium. The development medium typically contains nutrients that sustain the embryogenic tissue. Maltose may be included in the medium as the principal or sole source of sugar for the embryogenic tissue. Useful maltose concentrations are within the range of from about 1% to about 2.5%.

Suitable development media typically do not include growth-promoting hormones, such as auxins and cytokinins, but may include the hormone abscisic acid. When abscisic acid is utilized in the development medium, it is typically utilized at a concentration in the range of from about 1 mg/L to about 200 mg/L. The development medium may contain gellan gum, typically present at a concentration of up to about 0.35%. The osmolality of the development medium can be adjusted to a value that falls within a desired range, such as from about 250 mM/Kg to about 450 mM/Kg. Typically, an osmolality of 350 mM or higher is advantageous. An example of a suitable development medium is medium $BM_4$ set forth in EXAMPLE 1 herein.

Conifer embryogenic cells may be cultured in, or on, a development medium for a period of from 9 weeks to 14 weeks, such as from 10 week to 12 weeks, or such as about 12 weeks, at a temperature of from 10° C. to 30° C., such as from 15° C. to 25° C., or such as from 20° C. to 23° C.

In some embodiments, the present invention provides methods for producing conifer somatic embryos, the methods each including the steps of: (a) culturing conifer somatic cells in, or on, an induction medium to yield embryogenic cells; (b) culturing the embryogenic cells prepared in step (a) in, or on, a maintenance medium to multiply the embryogenic cells and form pre-cotyledonary conifer somatic embryos; (c) synchronizing the pre-cotyledonary conifer somatic embryos multiplied in step (b) in, or on, a synchronization medium that comprises an absorbent composition and at least one synchronization agent selected from the group consisting of abscisic acid and a gibberellin, wherein the absorbent composition and the synchronization agent(s) are each present at a concentration effective to produce a synchronized culture of pre-cotyledonary conifer somatic embryos; and (d) culturing the pre-cotyledonary conifer somatic embryos synchronized in step (c) in, or on, a development medium to yield a synchronized population of conifer cotyledonary somatic embryos.

The induction medium typically includes inorganic salts and organic nutrient materials. The osmolality of the induction medium is typically about 160 mg/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an absorbent composition, especially when very high levels of growth hormones are used. The absorbent composition can be any composition that is not toxic to the embryogenic cells at the concentrations utilized in the practice of the present methods, and that is capable of absorbing growth-promoting hormones, and toxic compounds produced by the plant cells during embryo development, that are present in the medium. Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from about 0.1 g/L to about 5 g/L.

An example of an induction medium useful in the practice of the present invention is medium $BM_1$, set forth in EXAMPLE 1 herein.

Conifer somatic cells are typically cultured in, or on, an induction medium for a period of from 6 weeks to 12 weeks, such as from 8 week to 10 weeks, or such as about 8 weeks, at a temperature of from 10° C. to 30° C., such as from 15° C. to 25° C., or such as from 20° C. to 23° C.

The maintenance medium may be a solid medium, or it may be a liquid medium which can be agitated to promote growth and multiplication of the embryogenic tissue. The osmolality of the maintenance medium is typically higher than the osmolality of the induction medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium. Examples of useful maltose concentrations are within the range of from about 1% to about 2.5%. An example of a suitable maintenance medium is medium $BM_2$ set forth in EXAMPLE 1 herein.

Conifer embryogenic cells are typically cultured in, or on, a maintenance medium for a period of up to 6 months by weekly subculture, at a temperature of from 10° C. to 30° C., such as from 15° C. to 25° C., or such as from 20° C. to 23° C.

Embryogenic cells are transferred from maintenance medium to a synchronization medium containing an absorbent composition and at least one synchronization agent selected from the group consisting of abscisic acid and a gibberellin, wherein the absorbent composition and the synchronization agent(s) are each present at a concentration effective to produce a synchronized culture of conifer somatic embryos. The composition of the synchronization medium may be the same as the maintenance medium, excluding growth hormones, but including an absorbent composition and at least one synchronization agent selected from the group consisting of abscisic acid and one or more gibberellins, as described above.

In some embodiments of the invention, an absorbent composition and at least one synchronization agent may be added directly to the maintenance medium that includes one or more growth-promoting hormones. The absorbent composition(s) bind growth-promoting hormones present in the medium so that the rate of multiplication of the embryogenic cells is reduced, or multiplication is stopped entirely, and the gibberellin(s) and abscisic acid promote production of a synchronized population of conifer somatic embryos. Thus, after the embryogenic cells have multiplied by a desired amount, an absorbent composition and at least one synchronization agent may be added to the maintenance medium (thereby converting the maintenance medium to a synchronization medium), or the embryogenic cells may be transferred to a synchronization medium containing an absorbent composition and at least one synchronization agent to yield synchronized conifer somatic embryos. The synchronized conifer somatic embryos may then be transferred to a development medium for synchronized cotyledonary embryo development, as described above.

In some embodiments, conifer cotyledonary somatic embryos produced according to the methods of the invention are cultivated in at least one maturation medium to generate mature conifer somatic embryos. A mature conifer somatic embryo according to the invention refers to an embryo that is capable of germinating into a plant.

The maturation medium medium can be a liquid or a solid medium. The maturation medium also may include nutrients that sustain the incubated cotyledonary embryos and/or maturing embryos, and one or more agents for adjusting the osmolality of the medium to within a desired range. The osmolality of the maturation medium is typically in the range of 250 to 450 mM/kg, such as about 350 mM/kg. The pH of the medium can also be adjusted to a desired value. The pH of the maturation medium is typically between about pH 5 and about pH 8, such as between about pH 5 and about pH 6. Maltose may be included in the medium as the principal or sole source of metabolizable sugar. Useful maltose concentrations are within the range of about 1% to about 2.5%. The maturation medium may contain an absorbent composition, such as activated charcoal, as described above for the induction medium.

Cotyledonary conifer somatic embryos are typically cultured in, or on, a maturation medium for a period of from 9 weeks to 14 weeks, such as from 10 week to 12 weeks, or such as about 12 weeks, at a temperature of from 10° C. to 30° C., such as from 15° C. to 25° C., or such as from 20° C. to 23° C.

In some embodiments, conifer somatic embryos are transferred to a stratification medium for a cold treatment prior to germination. Typically, the stratification medium is similar to development medium, but lacks abscisic acid, and typically does not include polyethylene glycol (PEG). An exemplary stratification medium is $BM_5$ set forth in EXAMPLE 1

Cotyledonary conifer somatic embryos are typically cultured in, or on, a stratification medium in the dark for a period of from 3 weeks to 6 weeks, such as about 4 weeks, at a temperature of from 1° C. to 10° C., such as from 1° C. to 8° C.

In some embodiments, the methods of the invention provide a synchronized population of conifer somatic embryos in which at least about 50% of the embryos are at the same developmental stage. In some embodiments, the methods of the invention provide a synchronized population of conifer somatic embryos in which at least about 80% of the embryos are at the same developmental stage. In some embodiments, the methods of the invention provide a synchronized population of conifer somatic embryos in which at least about 90% of the embryos are at the same developmental stage.

The methods of the invention produce a higher yield of conifer somatic embryos than an equivalent method in which the embryogenic cells are not cultivated in a synchronization medium. For example, according to the embodiment set forth in EXAMPLE 1, the yield is typically about 90 conifer somatic embryos per 100 mg (fresh weight) of cultured plant tissue in maturation medium. This contrasts with a yield of about 40 conifer somatic embryos per 100 mg (fresh weight) of cultured plant tissue in maturation medium, using an identical method that does not include the step of cultivating conifer embryogenic cells in, or on, a synchronization medium that comprises an absorbent composition and at last one synchronization agent selected from the group consisting of abscisic acid and gibberellins. Thus, some embodiments of the methods of the invention yield at least 100% more conifer somatic embryos (such as at least 150% more conifer somatic embryos, or such as at least 200% more conifer somatic embryos, or such as from 100% to 200% more conifer somatic embryos) than an identical method for producing conifer somatic embryos that does not include the step of cultivating conifer embryogenic cells in, or on, a synchronization medium that comprises an absorbent composition and at least one synchronization agent selected from the group consisting of abscisic acid and gibberellins.

The methods of the invention can be used, for example, to produce clones of individual conifer trees that possess one or more desirable characteristics, such as a rapid growth rate. Thus, in one aspect, the present invention provides methods for producing a population of genetically-identical, mature conifer somatic embryos. The methods of this aspect of the invention each include the step of cultivating embryogenic cells in a synchronization medium containing an absorbent composition and at least one synchronization agent selected from the group consisting of abscisic acid and at least one gibberellin. Any of the methods described herein can be used to produce populations of genetically-identical, mature somatic conifer embryos.

Another aspect of the invention provides mature conifer somatic embryos generated using the methods of the invention. The mature conifer somatic embryos produced using the methods of the invention can optionally be germinated to form conifer plants which can be grown into conifer trees, if desired. Alternatively, the mature embryos may be disposed within artificial seeds for subsequent germination. The mature conifer somatic embryos can be germinated, for example, on a solid germination medium, such as medium $BM_6$ medium set forth in EXAMPLE 1 herein. The germinated plants can be transferred to soil for further growth. For example, the germinated plants can be planted in soil in a greenhouse and allowed to grow before being transplanted to an outdoor site. Typically, the mature conifer somatic embryos are illuminated to stimulate germination. Typically, all the steps of the methods of the invention, except germination, are conducted in the dark.

The following examples merely illustrate the best mode now contemplated for practicing the invention, but should not be construed to limit the invention.

EXAMPLE 1

This Example shows a representative method for producing somatic pine embryos from loblolly pine.

Female gametophytes containing zygotic embryos were removed from seeds four to five weeks after fertilization. The seed coats were removed but the embryos were not further dissected out of the surrounding gametophyte other than to excise the nucellar end. The cones were stored at 4° C. until used. Immediately before removal of the immature embryos the seeds were sterilized utilizing an initial washing and detergent treatment followed by a ten minute sterilization in 15% $H_2O_2$. The explants were thoroughly washed with sterile distilled water after each treatment.

Tables 1 and 2 set forth the compositions of media useful for producing pine somatic embryos.

TABLE 1

| *Pinus Taeda* Basal Medium (BM) | |
|---|---|
| Constituent | Concentration (mg/L) |
| $NH_4NO_3$ | 150.0 |
| $KNO_3$ | 909.9 |

TABLE 1-continued

Pinus Taeda Basal Medium (BM)

| Constituent | Concentration (mg/L) |
|---|---|
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 30,000. |
| myo-Inositol | 200 |
| Casamino acids | 500 |
| L-Glutamine | 1000 |
| Thiamine•HCl | 1.00 |
| Pyridoxine•HCl | 0.50 |
| Nicotinic acid | 0.50 |
| Glycine | 2.00 |
| Gelrite[+] | 1600 |
| pH adjusted to 5.7 | |

[+]Used if a solid medium is desired.

TABLE 2

Composition of Media for Different Stage Treatments

| | |
|---|---|
| $BM_1$ - Induction Medium | BM + 2,4-D (15 μM) + Kinetin (2 μM) + BAP (2 μM). |
| $BM_2$ - Maintenance Medium | BM + 2,4-D (5 μM) + Kinetin (0.5 μM) + BAP (0.5 μM) Gelrite (1600 mg/L) is added when a solid medium is desired. |
| $BM_3$ - Synchronization Medium | BM + 250 mg/L activated charcoal + 10 mg/L abscisic acid + 10 mg/L GA4/7. Gelrite (1600 mg/L) is added when a solid medium is desired. |
| $BM_4$ - Development Medium | BM + 25 mg/L abscisic acid + 13% PEG-8000 + 800 mg/L additional myo-inositol + 0.1% activated charcoal. The following amino acid mixture is added: L-proline (100 mg/L), L-asparagine (100 mg/L), L-arginine (50 mg/L), L-alanine (20 mg/L), and L-serine (20 mg/L). Gelrite (2500 mg/L) is added when a solid medium is desired. |
| $BM_5$ - Stratification Medium | $BM_4$ modified by omitting abscisic acid, and PEG-8000. Maltose is increased to 2.5%. $FeSO_4.7H_2O$ is reduced to 13.9 mg/L and $Na_2EDTA$ is reduced to 18.6 mg/L. Gelrite (2500 mg/L) is added when a solid medium is desired. |
| $BM_6$ - Germination Medium | BM modified by replacing maltose with 2% sucrose. Myo-inositol is reduced to 100.0 mg/L, glutamine and casamino acids are reduced to 0.0 mg/L. $FeSO_4.7H_2O$ is reduced to 13.9 mg/L and $Na_2EDTA$ reduced to 18.6 mg/L. Agar at 0.8% and activated charcoal at 0.25% are added. |

Induction: Sterile gametophytes with intact embryos were placed on a solid $BM_1$ culture medium and held in an environment at 22°-25 C with a 24 hour dark photoperiod for a time of 3-5 weeks. The length of time depends on the particular genotype being cultured. At the end of this time a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 170 mM/kg. Normally it is about 160 mM/kg or even lower (such as 150 mM/kg).

Maintenance and Multiplication: Early stage embryos removed from the masses generated in the induction stage were first placed on a $BM_2$ gelled maintenance and multiplication medium. This differs from the induction medium in that the growth hormones (both auxins and cytokinins) are reduced by at least a full order of magnitude. Osmolality of this medium was typically raised from that of the induction medium to about 180 mM/kg or higher (typically within the range of about 180-400 mM/kg for Pinus taeda) by increasing the concentration of myo-inositol to 0.5% w/v. The temperature and photoperiod were again 22°-25 C with 24 hours in the dark. Embryos were cultured 12-14 days on the $BM_2$ solid medium before transferring to a liquid medium for further subculturing. This liquid medium has the same composition as $BM_2$, but lacks the gellant. The embryos at the end of the solid maintenance stage were typically similar in appearance to those from the induction stage. After 5 to 6 weekly subcultures on the liquid maintenance medium advanced early stage embryos have formed. These are characterized by smooth embryonal heads, estimated to typically have over 100 individual cells, with multiple suspensors.

Synchronization: Early stage embryos were transferred from induction medium or from maintenance medium into liquid or solid synchronization medium $BM_3$ for two weeks to yield synchronized early stage embryos. The synchronization medium has the same composition as $BM_2$, but lacks the hormones and contains activated charcoal, abscisic acid, and gibberellins.

Embryo Development: Synchronized early stage embryos were transferred to a solid development medium. The development medium either lacks growth hormones entirely, or has them present only at very low levels. Abscisic acid is typically included to facilitate further development. The further inclusion of an absorbent composition in this medium is advantageous. The absorbent composition may be chosen from a number of chemical materials having high surface area and/or controlled pore size, such as activated charcoal, soluble and insoluble forms of poly(vinyl pyrrolidone), activated alumina, and silica gel. The absorbent composition is normally present at a concentration of about 0.1-5 g/L, more generally about 0.25-2.5 g/L. Gellan gum was included at a concentration of about 0.25%.

The osmotic potential of this development medium may be raised substantially over that of the maintenance medium. It has been found advantageous to have an osmolality as high as 350 mM/kg or even higher. Development is preferably carried out in complete darkness at a temperature of 22°-25° C. until elongated cotyledonary embryos have developed. Development time is typically several weeks, such as 10 to 12 weeks.

Stratification: Cotyledonary embryos were singulated and transferred to stratification medium $BM_5$. This medium is similar to development medium but lacks abscisic acid, PEG-8000, and gellan gum. Embryos were cultivated on stratification medium at between about 1° C. and about 10° C. in the dark for between three to six weeks.

Drying: The mature embryos still on their filter paper support were lifted from the pad and placed in a closed container over a saturated solution of $K_2SO_4$, at a relative humidity of 97%, for a period of about three weeks.

Germination: The dried mature embryos were rehydrated by placing them, while still on the filter paper support, for about 24 hours on a pad saturated with liquid germination medium. The embryos were then placed individually on solid $BM_6$ medium for germination. This is a basal medium lacking growth hormones which has been modified by reducing sucrose, myo-inositol and organic nitrogen. The embryos were incubated on $BM_6$ medium for about 6-8 weeks under environmental conditions of 23°-25° C., and a 16 hour light-8 hour dark photoperiod, until the resulting plantlets have a well developed radicle and hypocotyl and green cotyledonary structure and epicotyl.

Because of the reduced carbohydrate concentration, the osmotic potential of the germination medium is further reduced below that of the development medium. It is normally below about 150 mM/kg (such as about 100 mM/kg).

EXAMPLE 2

This Example shows the effects of treatments of embryogenic cells with absorbent compositions, abscisic acid, and/or gibberellins prior to the development stage on the synchronization of development of Loblolly pine (*Pinus taeda*) somatic embryos.

Female gametophytes containing zygotic embryos were removed from seeds of genotype B and genotype A, as described in EXAMPLE 1. The induction and maintenance stages were as described in EXAMPLE 1.

To investigate the effects of treatments with absorbent compositions, abscisic acid, and/or gibberellins, 100 mg (fresh weight) of embryogenic cells were subjected to the following treatments for two weeks prior to transfer to development medium and continued development as described in EXAMPLE 1:

Control: embryos remained in standard maintenance medium containing hormones (2,4-D, Kinetin, and BAP, see EXAMPLE 1);

Treatment 1: embryos were transferred to maintenance medium without hormones and containing 250 mg/L activated charcoal (synchronization medium 1);

Treatment 2: embryos were transferred to maintenance medium minus hormones and containing 1 mg/L abscisic acid (synchronization medium 2);

Treatment 3: embryos were transferred to maintenance medium minus hormones and containing 250 mg/L activated charcoal and 5 mg/L abscisic acid (synchronization medium 3);

Treatment 4: embryos were transferred to maintenance medium minus hormones and containing 5 mg/L gibberellin GA4/7 (synchronization medium 4);

Treatment 5: embryos were transferred to maintenance medium minus hormones and containing 10 mg/L gibberellin GA4/7 (synchronization medium 5);

Treatment 6: embryos were transferred to maintenance medium minus hormones and containing 250 mg/L activated charcoal and 10 mg/L gibberellin GA4/7 (synchronization medium 6);

Treatment 7: embryos were transferred to maintenance medium minus hormones and containing 250 mg/L activated charcoal, 10 mg/L abscisic acid, and 10 mg/L gibberellin GA4/7 (synchronization medium 7, $BM_3$).

Cultures of early stage embryos were subjected to one of eight treatments for two weeks before transfer to development medium as described in EXAMPLE 1.

After 2 weeks, the effects of the treatments on embryo development were evaluated. For both genotypes tested, the control cultures were cleaving, growing, and forming embryo suspensor masses. The cultures contained large clumps and large embryo heads. Embryos were seen at different stages, showing no synchronization of culture.

The addition of activated charcoal to the maintenance medium in Treatment 1 (synchronization medium 1) slowed cleavage polyembryony but still allowed some embryo singulation. However, embryos started developing precociously, particularly in genotype B. The addition of a low concentration of abscisic acid to the maintenance medium (synchronization medium 2) inhibited precocious embryo development, but did not help to singulate the embryos. Embryos were seen in many different stages of development. The addition of both activated charcoal and abscisic acid (synchronization medium 3) inhibited precocious embryo development and greening, but allowed embryos to singulate and more uniformity in embryo size were seen in cultures with this treatment.

The addition of a low concentration of gibberellins (synchronization medium 4) also inhibited precocious embryo development and greening, but embryos were seen in many different stages. The addition of a higher concentration of gibberellins (synchronization medium 5) resulted in embryo greening.

The addition of activated charcoal and a low concentration of gibberellins (synchronization medium 6) cultures inhibited precocious embryo development and greening, and resulted in more uniformly sized embryos and more singulation than seen in control cultures. Finally, the addition of a combination of abscisic acid, gibberellins, and activated charcoal (synchronization medium 7) inhibited precocious embryo development and greening, while promoting singulation and synchronization of the cultures. The embryos in these cultures were very uniform in size compared to the control embryos.

Theses results show that singulation and uniform growth of early stage embryos before transfer to development medium can be achieved by pre-treating cultures in a synchronization medium containing activated charcoal and at least one of abscisic acid and a gibberellin. This treatment synchronized cotyledonary embryo development and maturation.

The embodiments of the invention in which an exclusive property or privilege is claimed are defined as follows:

1. A method for producing a synchronized population of pine somatic embryos, the method comprising:

(a) cultivating pre-cotyledonary pine embryogenic cells in, or on a maintenance medium comprising nutrients that sustain the pine embryogenic cells;

(b) cultivating pre-cotyledonary pine embryogenic cells from step (a) for a period from one week to two weeks in, or on, a synchronization medium that comprises maltose as the principal metabolizable sugar source, an absorbent composition and at least one synchronization agent selected from the group consisting of abscisic acid and a gibberellin, wherein the absorbent composition and the at least one synchronization agent are present at a concentration effective to produce a synchronized population of pre-cotyledonary pine somatic embryos wherein at least 50% of the pre-cotyledonary pine somatic embryos in the synchronized population are at the same developmental stage; and (c) transferring the synchronized population of pre-cotyledonary pine somatic embryos from step (b) to a development medium and culturing the pre-cotyledonary pine somatic embryos for a period from 9 to 14 weeks to produce a synchronized population of cotyledonary pine somatic embryos.

2. The method of claim 1 wherein the absorbent composition is selected from the group consisting of activated charcoal, soluble poly(vinyl pyrrolidone), insoluble poly(vinyl pyrrolidone), activated alumina, and silica gel.

3. The method of claim 2 wherein the absorbent composition is activated charcoal.

4. The method of claim 1 wherein the concentration of the absorbent composition in the synchronization medium is from about 0.5 g/L to about 50 g/L.

5. The method of claim 1 wherein the absorbent composition is activated charcoal, and the activated charcoal is present in the synchronization medium at a concentration in the range of from about 0.1 g/L to about 5 g/L.

6. The method of claim 1 wherein the absorbent composition is activated charcoal, and the activated charcoal is present in the synchronization medium at a concentration in the range of from about 0.5 g/L to about 1 g/L.

7. The method of claim 1, wherein abscisic acid is used as a synchronization agent.

8. The method of claim 1, wherein a gibberellin is used as a synchronization agent.

9. The method of claim 1, wherein abscisic acid and at least one gibberellin are used as synchronization agents.

10. The method of claim 1, wherein a gibberellin is present in the synchronization medium at a concentration of from about 0.5 mg/L to about 500 mg/L.

11. The method of claim 1, wherein a gibberellin is present in the synchronization medium at a concentration of from about 1.0 mg/L to about 100 mg/L.

12. The method of claim 1, wherein abscisic acid is present in the synchronization medium at a concentration of from about 1.0 mg/L to about 500 mg/L.

13. The method of claim 1, wherein abscisic acid is present in the synchronization medium at a concentration of from about 0.5 mg/L to about 20 mg/L.

14. The method of claim 1, wherein the osmolality of the synchronization medium is from about 90 mM/Kg to about 300 mM/Kg.

15. The method of claim 1, wherein the pH of the synchronization medium is from about 5 to about 6.

16. The method of claim 1, wherein Loblolly pine somatic embryos are produced from Loblolly pine embryogenic cells.

17. The method of claim 1, wherein at least 75% of the embryos in the synchronized population of pine somatic embryos are at the same developmental stage.

18. The method of claim 1, wherein the osmolality of the development media of step (c) is higher than the osmolality of the synchronization media of step (b).

19. The method of claim 1, wherein the osmolality of the synchronization media of step (b) is from about 90 mM/Kg to about 300 mM/Kg; and the osmolality of the development media of step (c) is from about 250 mM/Kg to about 450 mM/Kg.

20. The method of claim 1, wherein the synchronization medium of step (b) is a solid medium.

21. The method of claim 1, wherein the synchronization medium of step (b) is a liquid medium.

* * * * *